United States Patent

Nastke et al.

[11] Patent Number: 5,773,030
[45] Date of Patent: Jun. 30, 1998

[54] MULTIPLY-COATED PARTICLES

[75] Inventors: Rudolf Nastke, Rehbrücke, Germany; Ernst Neuenschwander, Riehen, Switzerland; Andreas Leonhardt, Freiburg, Germany

[73] Assignee: Novartis Corporation, Summit, N.J.

[21] Appl. No.: 532,551

[22] PCT Filed: Mar. 21, 1994

[86] PCT No.: PCT/EP94/00880

§ 371 Date: Sep. 29, 1995

§ 102(e) Date: Sep. 29, 1995

[87] PCT Pub. No.: WO94/22302

PCT Pub. Date: Oct. 13, 1994

[30] Foreign Application Priority Data

Apr. 1, 1993 [GB] United Kingdom ............... 9306852

[51] Int. Cl.$^6$ ............... A61K 9/16; A61K 9/50
[52] U.S. Cl. ............ 424/490; 424/489; 424/405; 424/486; 47/57.6
[58] Field of Search ............... 424/491, 490, 424/1–29, 405; 47/57.6; 71/118

[56] References Cited

U.S. PATENT DOCUMENTS 4,696,822  9/1987  Matsumura et al. ............... 424/490
4,938,797  7/1990  Hasslin et al. ............... 71/118
5,129,180  7/1992  Stewart ............... 47/57.6

FOREIGN PATENT DOCUMENTS 079668   5/1983   European Pat. Off. .
518263   12/1992  European Pat. Off. .
167769   10/1987  India .
8300799  3/1983   WIPO .
8903638  5/1989   WIPO .
9104661  4/1991   WIPO .

OTHER PUBLICATIONS

Journal of Controlled Release, 15 (1991), pp. 153–166.

*Primary Examiner*—Thurman K. Page
*Assistant Examiner*—William E. Benston, Jr.
*Attorney, Agent, or Firm*—Marla J. Mathias; William A. Teoli, Jr.

[57] ABSTRACT

Internally cross-linked albumin microspheres their surface being modified by attachment of polyoxy($C_?$)alkylene chains having a terminal ether group, especially such containing pharmacologically active agents, usable for pharmaceutical compositions.

11 Claims, 2 Drawing Sheets

MULTIPLY-COATED PARTICLES

This application is a 371 of PCT/EP94/00880 filed Mar. 21, 1994.

The present invention relates to multiply-coated biologically active particles, a process for preparing such coated particles and a method of using these particles in sustained-release formulations.

Encapsulation techniques are known and described, for example, in U.S. Pat. No. 4,938,797. The processes known to coat solid particulate active substances suffer from a number of disadvantages: due to the irregular geometry of particulate matter, coating is usually incomplete and the user risks skin-contact with the active substance. Furthermore, the problems of non-linear and/or incomplete release include environmental damage due to residual active substance, and unpredictable efficacy rates.

A process for the preparation of controlled release agrochemical granules is described in Indian patent specification 167769. In this process the active substance, embedded in a polyhydric polymer, represents only 3 to 31% by weight of the encapsulated granule. The release characteristics are shown by example to be non-linear.

P. G. Shukla et al. describe in J. Controlled Release, 15, p. 153 to 166 (1991) crosslinked starch-urea formaldehyde as a matrix for encapsulation of carbofuran. Release profiles of carbofuran are illustrated, however the amount of active substance is small, namely 3 to 20% by weight of the encapsulated particle, and the particle size is relatively large, ranging from 700 to 2000 $\mu$m. The rate of release of active substance is not constant, but follows an asymptotic course.

In U.S. Pat. 4,696,822 there are described compositions of mono-walled microencapsulated insecticides but the rate of release is not constant, falling after an initial burst.

In EP patent application 0 079668 A1 granules are described comprising the pesticide in a solid core, such core then being coated with at least one layer of a particular membrane selected from the group of dienes and an unsatturated fatty acid radical. The application of plural layers is also described each layer increasing the thickness of the coating, but no discrete phase boundary being formed between each layer.

Microencapsulated agricultural chemicals are described in published PCT application WO 91/04661. Microencapsulation by curing of a prepolymer may be accomplished in a single stage or in repeated stages. The polymer layers form a homogeneous coating which is a mono-coating since the repeated stages are carried out in the same reaction mixture by adding fresh hardener and/or prepolymer. The rate of release of active ingredient is rapid to begin with, but falls after an initial burst.

There is a need for a more efficient and predictable sustained-release delivery system for biologically active substances. A particular need is found in agriculture where the release characteristics of granular pesticide delivery systems tend to comprise a strong initial burst, followed by an ever-diminishing rate of release of the active substance. A constant rate of release can be illustrated graphically by a linear relationship between time and the amount of active substance released.

Coated granules are not sprayable. Microparticles, on the other hand, can be dispersed easily in water and are therefore sprayable, e.g. by the farmer or horticulturalist.

Surprisingly it has now been found that much-improved sustained release rates of active substance can be achieved with particulate, particularly microparticulate, biologically active substances coated by at least two layers of polymeric material in which there is a discrete phase-boundary formed between each coating layer and between the active substance and the first coating layer. The coating thus formed is heterogeneous since each successive layer is applied to a sub-layer around which a boundary surface has already formed. It has been found that in this way, high initial release rates of the prior art can be suppressed. This is especially useful when the active substance is a pesticide. Moreover handling safety is improved, and a reduced amount of coating material is achieved while effecting complete coating.

One object of the invention, therefore, is to provide encapsulated biologically active solid microparticles, each particle comprising i) a first discrete coating layer of a polymer which covers the surface of said particles partially or completely, and ii) at least one further discrete coating layer of the same polymer which covers the first layer and any exposed particle surface, wherein an inter-phase boundary is formed between the particle and the first coating layer and between the polymer layers, and the weight of each coating layer is from 1 to 30% of the average coated particle weight, and the sum of the weights of the coating layers is no greater than 40 % of the average coated particle weight.

The term microparticle is understood to include individually-coated discrete particles as well as coated clusters of at least two discrete particles, said clusters also being known as agglomerates.

The median microparticle diameter is preferably between 1 and 1000 $\mu$m, more preferably between 1 and 500 $\mu$m, most preferably 1 to 100 $\mu$m, and particularly preferred 3 to 50 $\mu$m.

The individual coating layer weight is preferably 2 to 25%, more preferably 5 to 20% and particularly preferred 5 to 15% of the coated particle.

The sum of the coating layer weights is preferably 5 to 40%, more preferably 5 to 30% and particularly preferred 10 to 20% of the coated particle weight.

The particle can be coated with two to four layers, preferably two layers.

Figure 1:
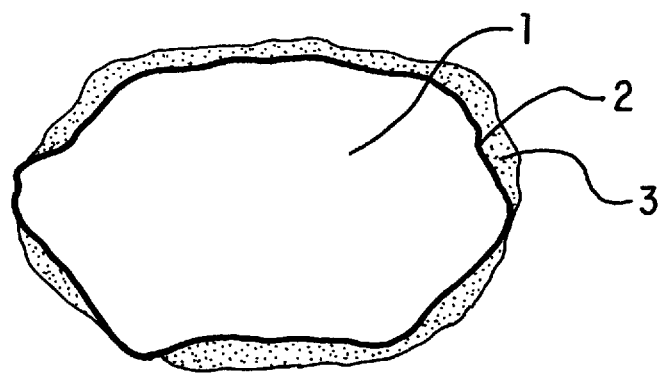
FIGS. 1 and 2 depict coated particles for sustained release according to the present invention.
Figure 2:
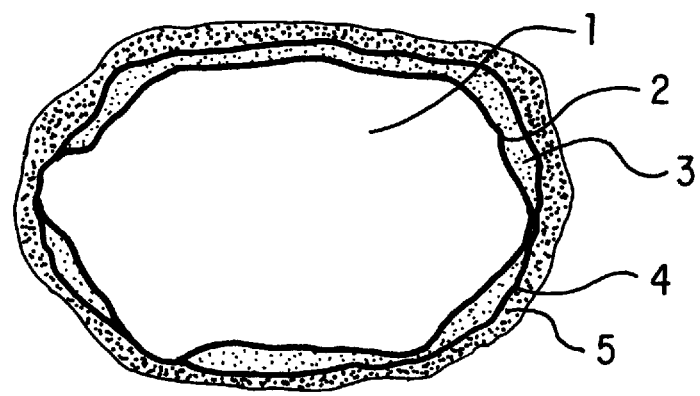

The coated particles according to the invention are illustrated in FIGS. 1 and 2.

In FIG. 1, region 1 represents the microparticulate active substance, region 2 represents the inter-phase boundary, and region 3 represents the first coating layer. The first coating layer covers the particle partially or completely. The inter-phase boundary represented by region 2 is correspondingly partial or complete.

In FIG. 2, region 1 represents the microparticulate active substance, region 3 the first discrete coating layer and region 5 the second discrete layer. Regions 2 and 4 represent inter-phase boundaries.

As is illustrated in FIGS. 1 and 2, the coverage of the first coating layer is typically incomplete, and there are uncoated areas on the particle. The second and optional subsequent discrete coatings envelop the particle completely.

The discrete phase-boundary surface between each coating layer can be identified by known surface-analysis methods, for example electron microscopy.

The active substance represents at least 60%, preferably from 60 to 95%, and more preferably 70 to 95% by weight of the coated particle mixture. Most preferred is 80 to 90% by weight active substance.

The biologically active substance is preferably a pesticide or mixture of pesticides, whereby the pesticide or pesticide mixture is solid at ambient temperature and substantially insoluble in water. The melting point of the active substance is preferably above 25° C. The particulate active substance remains solid in the coating process which is described below, i.e. the active substance does not melt during preparation of the coated microparticles.

The term pesticide is understood to encompass herbicides, insecticides, acaricides, nematicides, ectoparasiticides and fungicides. Examples of compound classes to which the pesticide in the practise of the invention may belong include ureas, triazines, triazoles, carbamates, phosphoric acid esters, dinitroanilines, morpholines, acylalanines, pyrethroids, benzilic acid esters and polycyclic halogenated hydrocarbons.

Specific examples of pesticides suitable for the coating process according to the invention are listed below (common names from The Pesticide Manual, 9th Edition, British Crop Protection Council):
Ureas
Chlorbromuron, Chloroxuron, Chlorotoluron, Fluometuron, Thiazafluron and Triasulfuron.
Haloacetanilides
Dimethachlor, Alachlor, Propachlor.
s-Triazines
Atrazine, Propazine, Terbuthylazine, Ametryn, Aziprotryne, Cyromazine.
Triazole derivatives
Etaconazole, 1-[2-(2,4-dichlorophenyl)-pent-1-yl]-1H-1,2, 4-triazole, Triadimefon, Difenoconazole.
Carbamates
Dioxacarb, Aldicarb, Benomyl.
Phosphoric acid ester
Methidathion, Anilofos, Azinphos methyl, Fenamiphos, Azamethiphos.
Dinitroanilines
Benfluralin, Pendimethalin, Butralin, Fluchloralin.
Acylalanines
Metalaxyl, Fluralaxyl, Benzoylprop ethyl, Flamprop methyl.
Pyrethroids
Cypermethrin, Resmethrin, Tetramethrin.
Benzilic acid esters
Bromopropylate, Chlorobenzilate, Chloropropylate.
Miscellaneous
Bromoxynil, Ioxynil, Oxadiazon, Dicofol, Fenoxycarb.

Preferred pesticides are Chlorotoluron, Atrazin or a compound of formula I

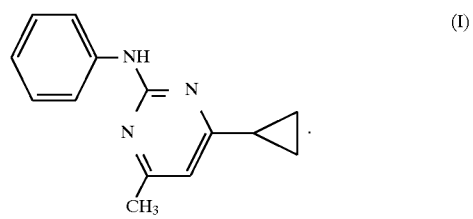

Each discrete coating layer around the particulate active substance is formed from the same polymeric material. Suitable polymers are well known in the art. Suitable polymeric materials in the practise of the invention can be structurally crosslinked polymers which are derived for example from aldehydes and phenols, ureas or melamines. Examples are phenol/formaldehyde resins, urea/formaldehyde resins and melamine/formaldehyde resins.

Preferred polymer coating layers are those which are biodegradable e.g. melamine-formaldehyde polymers, urea-formaldehyde polymers, polyurea, polyalkylglycols, polylactides, polyglycolides, natural polymers and mixtures of at least two of these polymers. Melamine/formaldehyde is most preferred. The molar ratio of melamine to formaldehyde can be between 1:2 and 1:8 and is preferably from 1:3 to 1:5.

Another object of the invention is a process for the preparation of coated microparticles by
i) forming an aqueous suspension, emulsion or solution A of a polymer or a polymer-forming precursor,
ii) combining this suspension, emulsion or solution with powder active substance,
iii) forming a suspension by high-speed stiring, and partially precipitating the polymer or polymer precursor on the microparticle surfaces and polymerising the polymer precursor,
iv) isolating the coated particles,
v) forming a dispersion of said coated particles in the aqueous suspension, emulsion or solution A,
vi) optionally repeating steps iv) and v) as many times as corresponds to the number of subsequent layers required, and
vii) isolating the coated microparticles.

Precipitation procedures depend in general on the nature of the polymers or polymer precursors used in the process. If polymer and/or precursor is dissolved in solvent, precipitation is effected for example in removing at least partially the solvent or in adding a non-solvent for the polymer of precursor. Precipitation may also be effected in changing the pH value, e.g. by acidification of the aqueous suspension, emulsion or solution. Precipitation of polymers may also be effected by interfacial polymerisation in adding a co-reactant to the precursor suspension, emulsion or solution.

Powder active substance is understood to include amorphous and crystalline forms.

As a general rule the rotation speed of the stirrer under high-speed stirring is typically from 3 to 16 m/sec, preferably from 4 to 8 m/sec, measured at the farthest point to the axis of rotation of the stirrer.

The isolation in steps iv) and vii) can be done by known methods, e.g. filtration, centrifugation or evaporation of moisture. At this stage it may be advantageous to dry the coated particles to obtain an improved surface quality.

The particles may be coated as a mixture of active substances or mixed after coating.

When two coatings are required, step vi) is omitted. In this way a first coating layer envelops the particulate active substance partially or completely and a second coating layer surrounds said first coating layer. Between the two coating layers there is a discrete inter-phase boundary. When three coatings are required, steps iv) and v) are repeated once.

A safener may be included in the coated particle mixture and may be coated together with the active substance or added after coating. It may be advantageous to include other additives in the mixture before or after coating, e.g. inert fillers, stabilisers, pigments, dyes, bait and repellants.

Another object of the invention is a composition containing discretely coated microparticles as active substances which may be dry, e.g. in powder form, or in the form of an aqueous dispersion.

The coated microparticle composition may be stored in a container prior to use. It may be advantageous to store the dry composition in a water-soluble bag or carton.

A further object of the invention is a method of treating plant growth deficiencies, pest attack in plants or animals, or nutrient-deficient soil by applying to the plant or animal locus a pesticidally and/or nutritionally effective amount of coated microparticulate active substance according to the invention or a composition comprising a mixture of active substances.

Other possible uses of the coated microparticles according to the invention are in water-treatment and hygiene.

The advantages of the microparticles according to the invention are as follows:

a) compositions of coated microparticles display more constant release rates of active substance(s);
b) there is a reduction in active substance necessary per unit area treated;
c) the active substance(s) can be mixed before or after coating;
d) the effectiveness of the active substance can be extended;
e) handling by users is safer than that of incompletely-coated particles, leading to reduced toxicological risk;
f) biologically degradable coatings can be used in agricultural applications;
g) contamination and waste through residue formation are avoided;
h) storage-stable and sprayable dispersions may be prepared; and
i) leaching is reduced.

The Examples below illustrate the invention in more detail. The measurement of release of the active substance is carried out as follows:

In order to provide ideal conditions under which the encapsulated active substance can release by diffusion through the capsule walls, the test method is conducted under "sink conditions". The formulation is dispersed in 1 liter of an aqueous medium in an amount such that complete release of the active ingredient leads to a concentration in the solution of 10% of the solubility of the active ingredient. This dispersion is stirred gently without applying mechanical stress on the capsules. Filtered samples of the medium are taken at regular time intervals and analysed directly with respect to the active content by HPLC or GLC.

Since the active ingredient is only sparingly soluble in water, a mixture of buffer and surfactant solution in water can be used as release medium. The release medium used for chlorotoluron with a water solubility of 70 ppm can be, for example, a solution of 3% TWEEN-20 in dilute phosphate buffer pH 7. TWEEN-20, available commercially from ICI, is a nonionic surfactant comprising a sorbitan ester with 20 ethylene oxide units.

PREPARATIVE EXAMPLES

Example 1: illustrates a known method with an encapsulation part of 22 weight %

12.5 g chlorotoluron are dispersed in 50 ml water. To this dispersion are added 15.5 ml of a 50 weight-% aqueous solution of a melamine(M)-formaldehyde(F) prepolymer (M:F molar ratio 1:3) partially etherified with methanol, and a suspension formed using a high-speed dissolver stirrer. While maintaining the same stirring speed, the suspension is heated to 60° C. and 7.0 ml 2N citric acid are added. The suspension is stirred for a further 2 hours, cooled to room temperature and filtered. The filter cake is washed with 50 ml water and vacuum-dried at 60° C. There results a fine white powder with median particle diameter of 2 to 10 $\mu$m.

The median particle diameter (MPD) is measured by laser light diffraction using a Cilas Granulometer.

Example 2: illustrates a known method with an encapsulation part of 30 weight %

12.5 g chlorotoluron are dispersed in 50 ml water. To this dispersion are added 10.5 ml of a 50 weight-% aqueous solution of a melamine (M)-formaldehyde (F) prepolymer (M:F molar ratio 1:3) partially etherified with methanol, and a suspension formed using a high-speed dissolver stirrer. While maintaining the same stirring speed, the suspension is heated to 60° C. and 7.0 ml 2N citric acid are added. The suspension is stirred for a further 2 hours and cooled to room temperature. Then a solution containing 50 ml water and 10.5 ml of the 50 weight-% M/F-resin aqueous solution is added to the suspension using high speed stirring. While maintaining the same stirring speed, the suspension is heated to 60° C. and 7.0 ml 2N citric acid are added. The suspension is stirred for a further 2 hours, cooled to room temperature and filtered. The filter cake is washed with 50 ml water and vacuum-dried at 60° C. There results a fine white powder with median particle diameter of 5 to 15 $\mu$m.

Example 3: inventive process with an encapsulation part of 22 weight %

12.5 g chlorotoluron are dispersed in 50 ml water. To this dispersion are added 10.5 ml of a 50 weight-% aqueous solution of a melamine (M)-formaldehyde (F) prepolymer (M:F molar ratio 1:3) partially etherified with methanol, and a suspension formed using a high-speed dissolver stirrer. While maintaining the same stirring speed, the suspension is heated to 60° C. and 7.0 ml 2N citric acid are added. The suspension is stirred for a further 2 hours, cooled to room temperature and filtered. Then the filtercake is combined with a solution of 50 ml water and 5 ml of the 50 weight-% M/F-resin aqueous solution using high-speed stirring. While maintaining the same stirring speed, the suspension is heated to 60° C. and 7.0 ml 2N citric acid are added. The suspension is stirred for a further 2 hours, cooled to room temperature and filtered. The filtercake is washed with 50 ml water and vacuum-dried at 60° C. There results a fine white powder with median particle diameter of 5 to 15 $\mu$.

Example 4: inventive process with an encapsulation part of 30 weight %

The procedure is followed as for Example 3 but in the second encapsulation step 10.5 ml of the 50 weight-% M/F resin aqueous solution are added. There results a fine white powder with median particle diameter of 5 to 20 $\mu$m.

Application Examples

Figure 3:
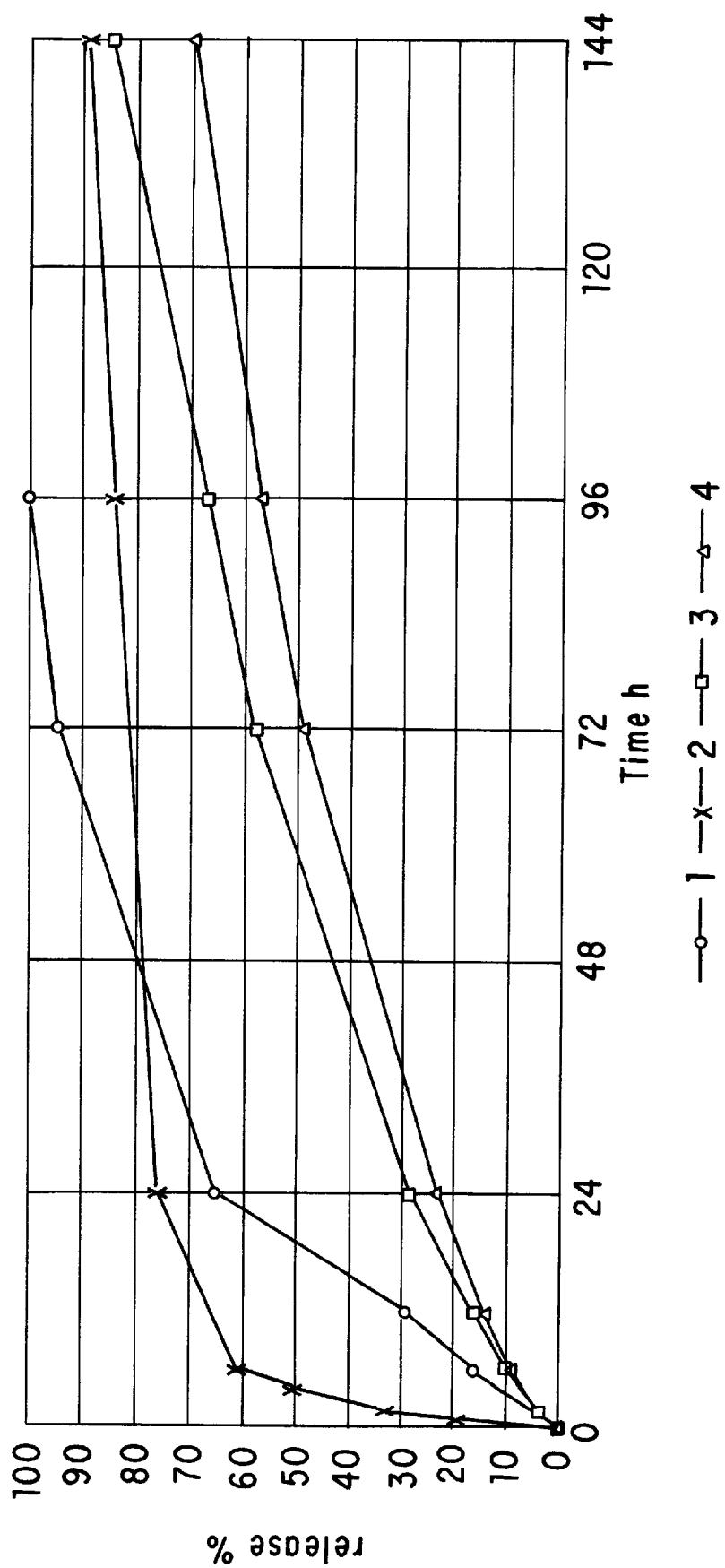
FIG. 3 represents a graph of the percent release of active ingredient versus time in hours.

The release characteristics of the microparticles prepared in the above Examples are illustrated graphically on FIG. 3 by graphs 1,2,3 and 4 corresponding to Examples 1,2, 3 and 4 respectively. The graphs in FIG. 3 show % release of active ingredient plotted against time in hours.

What is claimed is:

1. Encapsulated microparticles of a pesticide or mixture of pesticides, whereby the pesticide or pesticide mixture is solid at ambient temperature and substantially insoluble in water, each particle comprising i) a first discrete coating layer of a polymer which covers the surface of said particles partially of completely, and
ii) at least one further coating layer of the same polymer which covers the first layer and any exposed particle surface, wherein an inter-phase boundary is formed between the particle and the first coating layer and between the polymer layers, and the weight of each coating layer is from 1 to 30% of the average coated particle weight, and the sum of the weights of the coating layers is no greater than 40% of the average coated particle weight wherein the median microparticle diameter is between 1 and 1000 $\mu$m.

2. Encapsulated microparticles according to claim 1, wherein the individual coating layer weight is 2 to 25% of the coated particle.

3. Encapsulated microparticles according to claim 1, wherein the sum of the coating layer weights is from 5 to 40% of the coated particle weight.

4. Encapsulated microparticles according to claim 1, wherein the particles are coated with two to four layers.

5. Encapsulated microparticles according to claim 1, wherein the active substance represents from 60 to 95% by weight of the coated particle mixture.

6. Encapsulated microparticles according to claim 1, wherein the active substances are herbicides, insecticides, acaricides, nematicides, ectoparasiticides or fungicides.

7. Encapsulated microparticles according to claim 1, wherein the active substances are Chlorotoluron, Atrazin or a compound of formula I

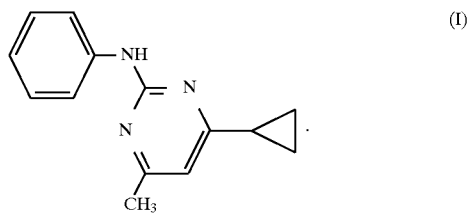

(I)

8. Encapsulated microparticles according to claim 1, wherein the polymer coating layers are melamine-formaldehyde polymers, urea-formaldehyde polymers, polyurea, polyalkylglycols, polylactides, polyglycolides, natural polymers or mixtures of at least two of these polymers.

9. A process for the preparation of coated microparticles according to claim 1 by
   i) forming an aqueous suspension, emulsion or solution A of a polymer or a polymer-forming precursor,
   ii) combining this suspension, emulsion or solution with powder active substance,
   iii) forming a suspension by high-speed stirring, and partially precipitating the polymer or polymer precursor on the microparticle surfaces and polymerising the polymer precursor,
   iv) isolating the coated particles,
   v) forming a dispersion of said coated particles in the aqueous suspension, emulsion or solution A,
   vi) optionally repeating steps iv) and v) as many times as corresponds to the number of subsequent layers required, and
   vii) isolating the coated microparticles.

10. A composition containing discretely coated microparticles according to claim 1 which is dry or in the form of an aqueous dispersion.

11. A method of treating plant growth deficiencies, pest attack in plants or animals, or nutrient-deficient soil by applying to the plant or animal locus a pesticidally and/or nutritionally effective amount of coated microparticulate active substance or a composition comprising a mixture of active substances.

* * * * *